United States Patent [19]

Login et al.

[11] Patent Number: 4,801,400
[45] Date of Patent: Jan. 31, 1989

[54] EPOXY PYRROLIDONE BASED NON-IONIC SURFACTANTS

[75] Inventors: Robert B. Login, Oakland; Mohamed M. Hashem, Wayne; David J. Tracy, Lincoln Park, all of N.J.

[73] Assignee: GAF Corporation, Wayne, N.J.

[21] Appl. No.: 21,053

[22] Filed: Mar. 2, 1987

[51] Int. Cl.$^4$ .................. C07D 403/12; C07D 403/14; B01F 17/22; B01F 17/32
[52] U.S. Cl. ..................... 252/357; 252/358; 252/363.5; 252/311; 252/320; 252/321; 548/517; 548/519; 548/543; 71/DIG. 1
[58] Field of Search ................ 548/519; 252/311, 320, 252/321, 357, 358, 363.5

[56] References Cited

U.S. PATENT DOCUMENTS 3,136,766  6/1964  Buc et al. .......................... 252/357
4,698,412 10/1987  Tracy et al. ....................... 548/519

Primary Examiner—Donald G. Daus
Assistant Examiner—E. Bernhardt
Attorney, Agent, or Firm—Marilyn J. Maue; Joshua J. Ward

[57] ABSTRACT

The invention relates to compounds having the formula:

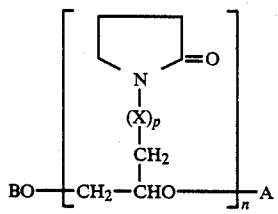

wherein
X is $-(CH_2)_s-$ or $-(CH_2)_s-O-$;

B is $C_{8-24}$ alkyl—;

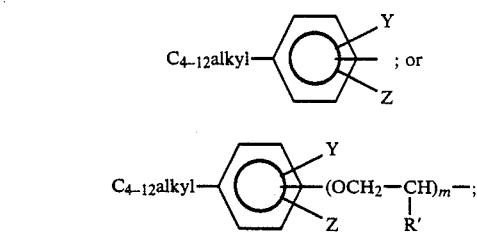

Y and Z are each H or $C_{1-12}$ alkyl;
m is an integer having a value of 1 to 100;
n is an integer having a value of 2 to 50;
p is an integer having a value of 0 or 1;
s is an integer having a value of 1 or 2;
R' is H or $CH_3$ and
A is H or

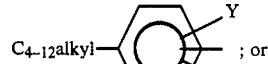

wherein R" is hydrogen or methyl and r is an integer having a value of from 1 to 100.

The invention also relates to the process for the preparation of said compounds, as well as the process of using them as a surfactant or complexing agent and compositions therefor.

10 Claims, No Drawings

EPOXY PYRROLIDONE BASED NON-IONIC SURFACTANTS

In one aspect, the invention relates to a new class of non-ionic compounds having superior surfactant properties.

In another aspect the invention relates to the use and preparation of novel nonionic surfactants.

The compounds of this invention are characterized by containing within their structure a plurality of hydrophilic pyrrolidone units which are chemically bonded to a hydrophobic moiety in the form of a telomer. Due to the spacial arrangement of the functional groups, especially the orientation of the molecule resulting from spacial separation of hydrophobic and hydrophilic groups in the telomer structure, these compounds possess unique and advantageous properties that distinguish them from prior surfactant compounds. The excellent solvent and complexing properties of the poly-(alkoxylated pyrrolidone) moiety provides compounds which are useful as wetting agents, emulsifying agents and other surfactant applications beneficially applied in the solubilization and complexation of insoluble compounds, which due to their nontoxic character, make them particularly valuable for solubilizing drugs, cosmetics and agricultural chemicals. The novel telomers of the invention also find application in the separation of biologically active molecules from fermentation broths and other media.

It is an object of the present invention to provide a group of novel compounds having unique properties.

Another object of the invention is to provide a novel and improved surfactant and complexing agent.

Another object of this invention is to provide a method for the preparation for said compounds by an economical and commercially feasible process.

Still another object is to provide a surfactant having alterable hydrophobic-hydrophilic balance tailored to meet a specific need.

Yet another object is to provide proesses for using said compounds.

These and other objects will become apparent from the following description and disclosure.

THE INVENTION

According to this invention there is provided a compound having the formula:

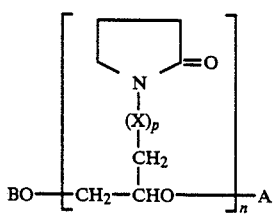
1.

wherein
X is $$-(CH_2)_s- \text{ or } -(CH_2)_s-O-;$$

B is $C_{8-24}$ alkyl-;

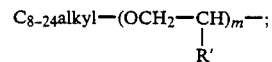

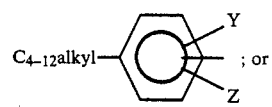

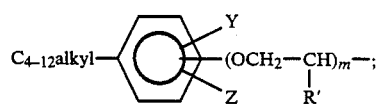

Y and Z are each H or $C_{1-12}$ alkyl:
m is an integer having a value of 1 to 100; n is an integer having a value of 2 to 50; p is an integer having a value of 0 or 1; s is an integer having a value of 1 or 2;
R' is H or $CH_3$ and A is H or

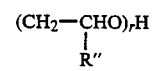

wherein R'' is hydrogen or methyl and r is an integer having a value of from 1 to 100.

Compounds of the above type possess excellent surfactant properties such that as little as 0.01% in distilled water at 25° C. is sufficient to lower the surface tension from about 72 to 30 or less dynes/cm.

Of the above, compounds having the structure

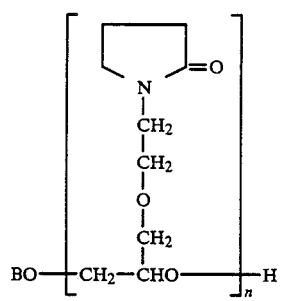
2.

wherein B is alkyl having from 8 to 22 carbon atoms or $C_8$ to $C_{b\ 12}$ alkyl phenyl wherein phenyl is optionally substituted with up to two alkyl groups containing from 1 to 12 carbon atoms and wherein the number (n) of hydrophilic lactam moieties approximately balances the hydrophobic effect of the B moiety, are preferred and the derivative where B is dodecanol is most preferred for surfactant purposes.

The polymers wherein n is 8 or more present numerous complexing sites for incorporating relatively larger amounts of medicinal or biologically reactive compounds in a complexed structure.

Additionally, the species of this invention containing polymeric blocks of the alkoxy pyrrolidone units and/or blocks of 3–50 units of ethylene oxide and/or blocks of 3–50 units of propylene oxide are additionally valuable as low foaming agents which may be incorporated into detergent formulations, etching baths, coating compositions, pesticide and germicide formulations and the ike in an amount of between about 0.1 and about 10 weight %.

Block copolymeric products are illustrated by the following formulae

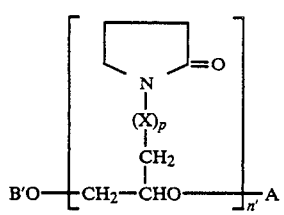

wherein B' is

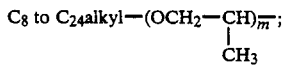
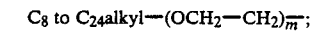
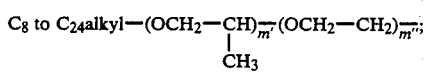
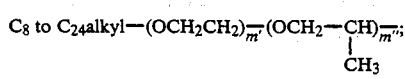
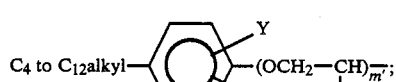
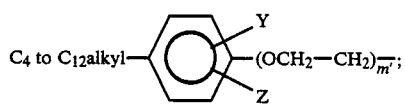
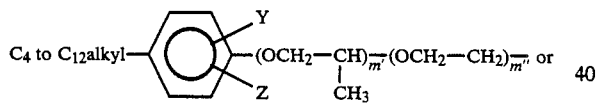
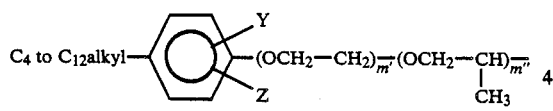

wherein m in the above formulae 3 has a value of 5 to 100 preferably from 5 to 20 and m', and m" each have a value of from 3 to 50, preferable from 5 to 20.

The block copolymers may also have the formula

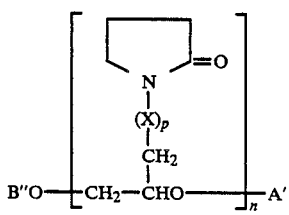

wherein B" is

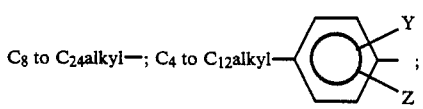

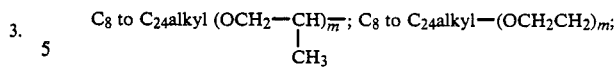
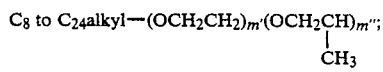
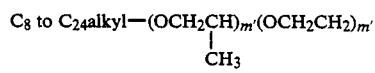
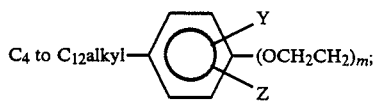
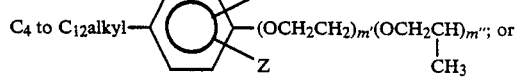
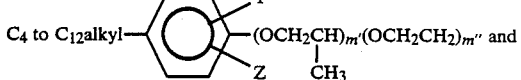

A' is 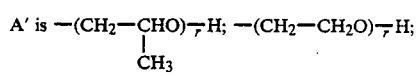

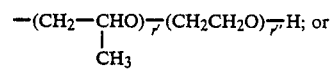

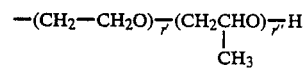

wherein r has a value of from 5 to 100, preferably from 5 to 20 and r', and r" each independently have a value of from 3 to 50, preferably 5 to 20.

The compounds of this invention can be prepared by similarly simple and commercially feasible processes which provide product in high yield. One method for their preparation of compounds having the formula

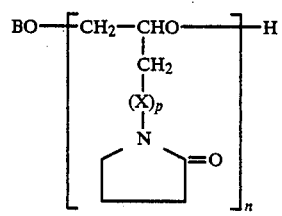

involves reacting an epoxyalkyl pyrrolidone having the formula

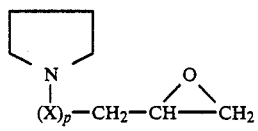

with an alcohol having the formula

BOA where B and A are as defined above. Specifically, B can be

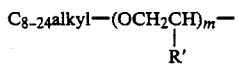

wherein the expression

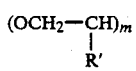

can represent a single unit, a single unit of each of (OCH$_2$CH$_2$ and (OCH$_2$CH)
 |
 CH$_3$ or a radical having units of (OCH$_2$—CH$_2$)$_{m'}$ and/or

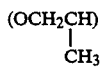

in a block structure wherein at least one of m' or m'' is an integer greater than one, preferably 3 to 50. Alternatively B can be

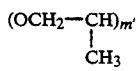

wherein the expression

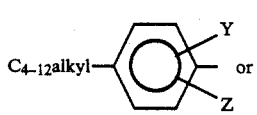

can represent a single unit, a single unit of each of (OCH$_2$CH$_2$) and (OCH$_2$—CH)
 |
 CH$_3$ or a radical having units of (OCH$_2$CH$_2$)$_{m'}$ and/or

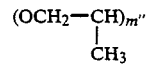

in a block structure wherein at least one of m' or m'' is an integer greater than one, preferably 3 to 50.

The epoxyalkyl pyrrolidone is gradually added to the alcohol after removal of water and the resulting reaction mixture is subjected to agitation under anhydrous and basic conditions at a temperature below the decomposition temperature of the desired condensation product of the process, e.g. a temperature between about 120° C. and about 160° C. for a period of from about 1 to about 12 hours, preferably from about 1.5 to about 5 hours under a pressure of from about 14 psig to about 100 psig. After the reaction is completed, the reaction mixture is cooled and neutralized to provide the product of this invention in quantitative yield and in an anhydrous state.

A process which can be employed for the preparation of products having the formula

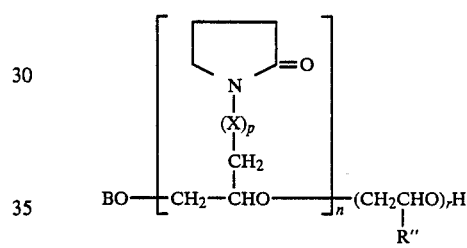

may be carried out in two stages wherein the product of the process recited above is recovered and reacted with r moles of an epoxide of the formula

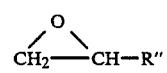

wherein R'' is H or CH$_3$', and r is an integer having a value of from 1 to 100 at substantially a temperature in the same range but at superatmospheric pressure, e.g. a pressure of between about 25 and about 100 psig.

Additionally, a process for preparing products having the formula

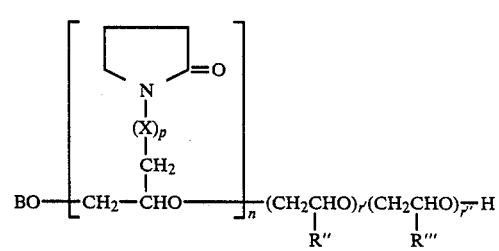

wherein one of R'' and R''', is hydrogen and the other is methyl and r' and r'' each have a value of from 1 to 50, involves reacting the product

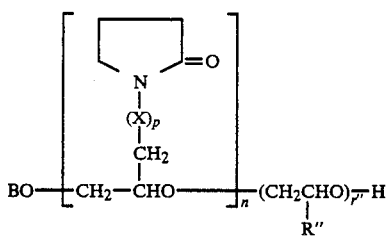

with r″ moles of an epoxide having the formula

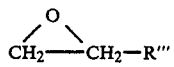

at a similar temperature, under superatmospheric pressure up to about 100 psig.

Although many preparations of the eppoxyalkyl pyrrolidone starting material are known, the method which has been employed for the purpose of the present invention includes the reaction between an epihalohydrin and the alkali metal salt of 2-pyrrolidone according to the equation:

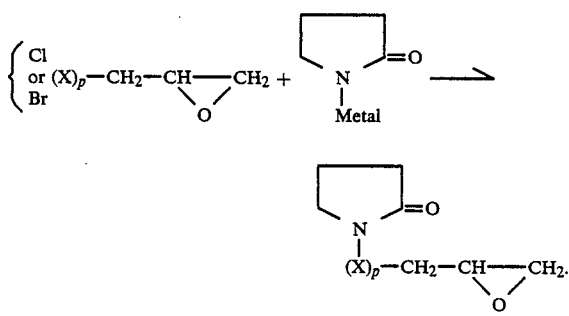

This reaction is generally effected in the liquid phase in the presence of an inert solvent, such as toluene, benzene, ether etc. at a temperature maintained between about 50° and about 100° C. under atmospheric or increased pressure for example 2–3 atmospheres; for a period of from about 0.5 to about 5 hours. The resulting alkali metal halide (chloride or bromide) by-product is removed by filtration and solvent is stripped from the product under vacuum, after which the epoxyalkyl pyrrolidone can be further purified by distillation.

While the process described above is recommended, it is to be understood that it is merely representative of those known in the art which may be equally suitable for obtaining the epoxyalkyl pyrrolidone reactants of the present invention. The following equations illustrate other suitable reactions which can be carried out at similar temperature and pressure conditions for the preparation of the present monomeric starting materials.

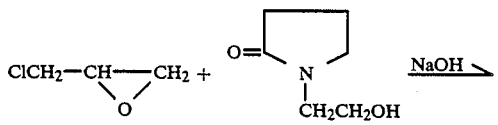

-continued

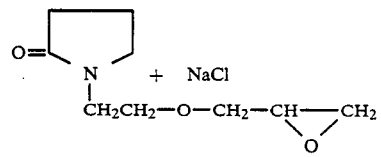

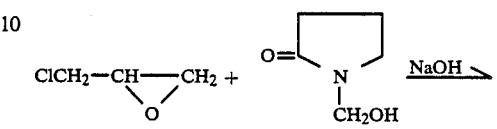

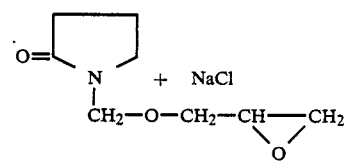

Several methods for the preparation of the BOH coreactant in the above condensation reaction are also known. A preferred method for the preparation of coreactant having a B moiety containing units of $(OCH_2-CH_2)_{m'}$ and

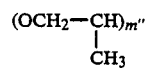

wherein at least one of $m'$ or $m''$ is an integer greater than one comprises reacting an alcohol having the formula

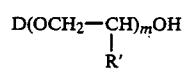

with an epoxide having the formula

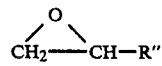

wherein one of R′ and R″ is hydrogen and the other is methyl. This reaction is effected at a temperature of between about 75° C. and about 200° C. for a period of from 30 minutes to 12 hours and the product of this reaction is defined by the formula

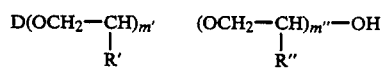

wherein one of R′ and R″ is hydrogen and the other is methyl and D is C8–24 alkyl- or

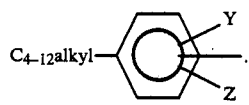

As stated above, the products of the present invention have excellent surfactant and complexing properties and are therefore useful in solubilizing various insoluble chemicals and chemical compositions. Broadly, for the solubilization and/or complexing applications, between about 0.001 wt. % and about 50 wt. % of the present telomers in an inert carrier or in a dry state can be added to the insoluble compound. More specifically, between about 0.01 wt. % and about 20 wt. % of the present compounds are incorporated into shampoo, hair conditioning, cosmetic cream and lotion formulations for longer shelf life and additional wetting and moisturizing properties. Representative of such formulations are:

| Ingredient | % by wt. |
|---|---|
| Shampoo | |
| $C_{14}$–$C_{16}$ Alpha Olefin Sulfonate | 20.00 |
| Ammonium Lauryl Sulfate | 25.00 |
| Cocamidopropyl Betaine | 3.50 |
| Reaction product of nonylphenol with 2 moles of N—epoxypropylpyrrolidone | 1.00 |
| Sodium Laureth-4-Phosphate | 1.00 |
| Hydrolyzed Animal Protein | 0.25 |
| $Na_4$ EDTA | 0.15 |
| Deionized Water | Q.S. |
| Fragrance | Q.S. |
| Preservative | Q.S. |
| Skin Care Lotion | |
| Stearic Acid | 3.00 |
| Mineral Oil | 2.00 |
| Emulsifying Wax | 3.00 |
| Dimethicone | 1.50 |
| Deionized Water | Q.S. |
| Carbomer 934[1] | 0.15 |
| Oleth-20[2] | 1.00 |
| Reaction product of nonyl phenol-3-propylene oxide adduct with 4 moles of N—epoxypropyl pyrrolidone | 1.00 |
| Triethanolamine, 98% | 1.00 |
| Preservative | Q.S. |
| Fragrance | Q.S. |
| Facial Cream | |
| Mineral oil, 70 cts | 6.00 |
| Petrolatum | 4.00 |
| Lanolin | 3.00 |
| Glyceryl Monostearate, S.E. Acid Stable | 19.00 |
| Glycerine | 1.00 |
| Reaction product of Dodecanol with 3 moles of N—epoxypropyl pyrrolidone | 2.00 |
| Deionized water | Q.S. |
| Preservative | Q.S. |
| Fragrance | Q.S. |

The present products can also exhibit good low foaming properties, particularly when the molecule contains a substantial amount of polypropyleneoxy units, and are therefore useful ingredients in detergent formulations and etching baths. A particular detergent formulation is represented by

| | |
|---|---|
| Sodium tripolyphosphate | 50.00 |
| Sodium silicate | 10.00 |
| Sodium sulfate | 17.50 |
| Nonyl phenol + 6 units N—propoxy-2-pyrrolidone | 17.50 |
| $H_2O$ | 5.0 |

[1] a polymer of acrylic acid crosslinked with a polyfunctional agent
[2] the polyethylene glycol ether of oleyl alcohol having the formula: $CH_3(CH_2)_7CH=CH(CH_2)_7CH_2(OCH_2CH_2)_{av20}OH$ Grimy dirt and greasy sebum are easily removed by 1 cycle washing (15 minutes and 5 minute rinse) using this formulation at 80° F.

The products of the present process are also useful in many other applications. For example, they can be used to retain fragrances in e.g. perfumes, cosmetics and agricultural products. They will interact with irritating or noxious components such as radioactive moieties, cyano compounds and others to form complexes which are less harmful. Their complexing ability also makes them useful in agricultural, pharmaceutical and medical applications for controlled release of drugs, vitamins, germicides, herbicides, plant growth regulants etc., and in the area of clarification of beverages and water, blood purification removal of water soluble or oil soluble stains from textiles, decaffinization, extractants for antibiotics in fermentation broths for shale oil removal, for dehydrating fuels etc. The penetrating power of the present products makes them excellent dermal and membrane transport agents and household detergents.

Other fields of application are outlined as follows:

| PHARMACEUTICAL/ MEDICAL | WASTE MANAGEMENT |
|---|---|
| Blood Substitute | Complex heavy metals |
| Foam stabilizer | Complex Organics |
| | Remove pollutants from aqueous phase |
| AGRICULTURAL | ELECTRONICS |
| Frost Protection | Metal dispersant for recording tape |
| Solubilize active ingredients | Corrosion inhibition |
| | Clean circuit boards |
| MILITARY | Dielectric in capacitors |
| Aerial and topical decontamination | Solder Flux |
| TEXTILE | METAL COATINGS |
| Dye assist agent | Corrosion inhibition |
| Dye removal/solubilization | Metal cleaning |
| | Metal quenching in sintering |
| | Degreasing |
| | Paint-emulsion polyerization |
| BIOTECHNOLOGY | OIL AND GAS |
| Solubilize enzymes in organic phase | Coal oil slurries |
| | Oil based drilling muds |
| Cleaning exchange columns Exchange resin with polymer anchor Phase transfer | Corrosion inhibition |
| PLASTICS | HOUSEHOLD |
| Processing aid | Odor control |
| (slip and release) | Detergents |
| Increase dye acceptance | Pool chemicals |
| High temperature antistant | |

Also the water solubility of valuable agricultural chemicals such as Lasso, Blazer, Seven, Treflan, Sutan, etc. can be greatly improved by incorporation of from about 0.01 wt. % to about 10 wt. % of the present compounds into their formulations.

The present surfactant products can be added to the above formulations in neat form or as a solution in water or in any inert organic solvent including glycols, alcohols, ketones, ethers or the like.

Complexes of the present products with various water insoluble compounds are also readily prepared. For example, mixture of the surfactant with a drug, e.g., aminobenzoic acid, in a weight ratio of from about 10:1 to about 2:1 results in a water soluble complex which is suitable for administration by injection. Many other veterinarian and medical uses for the present products will become apparent from this disclosure.

Having generally described the invention, reference is now had to the follwing examples which set forth preferred embodiments included herein but which are not to be construed as limiting to the scope of the invention as more broadly set forth above and in the appended claims.

EXAMPLE 1

PREPARATION OF EPOXYPROPYL PYRROLIDONE

To a 5 liter flask equipped with a stirrer, condenser, thermometer and dropping funnel was charged 604 g. (4.28 moles) epibromohydrin and 2150 ml. of ethyleneglycol dimethylether. To this solution was added, over a half hour period, 263.5 g. (2.14 moles) potassium pyrrolidone. The mixture was stirred 48 hours at 25° C. Potassium bromide was removed by filtration and the product distilled. The fraction boiling at 87° to 100° at 0.07 to 0.1 mm Hg was collected as 201.8 g. of product (67% of Theory) having a purity of 93% analyzed by gas chromatography. The reaction of this example can be described by the equation:

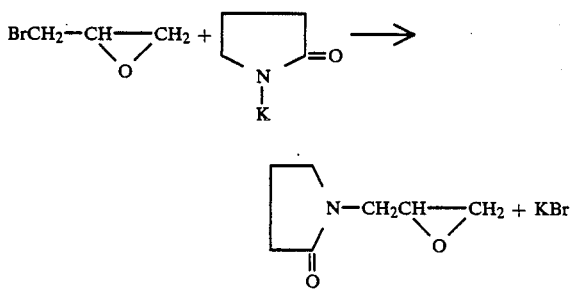

EXAMPLE 2

Reaction Product of Nonylphenol with 2 Moles Epoxypropyl Pyrrolidone

To a 500 ml. round bottom flask equipped with a reflux condenser, stirrer, dropping funnel, and nitrogen bubbler was charged 87.0 g. (0.39M) nonylphenol and 0.1 g. of powdered potassium hydroxide. The mixture was heated to 110° to 120° C. with a nitrogen purge to remove water. The purge was carried out prior to placing the condenser on the reactor. The temperature was held at 110° to 120° C. for 2 hours under the nitrogen purge. Epoxypropyl pyrrolidone 112.0 g. (0.79M) was added dropwise over a 2-hour period, holding the temperature at 130° to 135° C. The reaction was held at 130° to 140° C. for two hours after the addition was completed. Vapor phase chromatography indicated the absence of epoxypropyl pyrrolidone and nonylphenol. The reaction mixture was cooled to 65° C. and neutralized with glacial acetic acid. The product was cloudy in water and had a cloud point below zero. Analysis by % OH indicated 1.2 moles reacted. Analysis by ultraviolet spectra indicated 1.4 moles reacted.

The product of this example has the formla

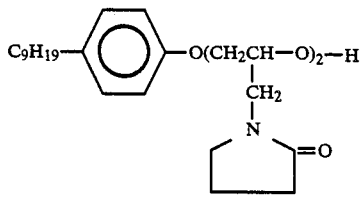

EXAMPLE 3

Reaction Product of Nonylphenol with 4 Moles Epoxypropyl Pyrrolidone

To a 500 ml. round bottom flask equipped with a reflux condenser, stirrer, dropping funnel, and nitrogen bubbler was charged 87.0 g. (0.39M) nonylphenol and 0.1 g. of powdered potassium hydroxide. The mixture was heated to 110° to 120° C. with a nitrogen purge to remove water. The purge was carried out prior to placing the condenser on the reactor. The temperature was held at 110° to 120° C. for 2 hours under the nitrogen purge. Epoxypropyl pyrrolidone 222.8 g. (1.58M) was added dropwise over a 2-hour period, holding the temperature at 130° to 135° C. The reaction was held at 130° to 140° C. for two hours after the addition was completed. Vapor phase chromatography indicated the absence of epoxypropyl pyrrolidone and nonylphenol. The reaction mixture was cooled to 65° C. and neutralized with glacial acetic acid. The product was clear in water and had a cloud point of 33° C. (1% in water). Analysis by ultraviolet indicated 3.8 moles reacted.

The product is defined by the formula:

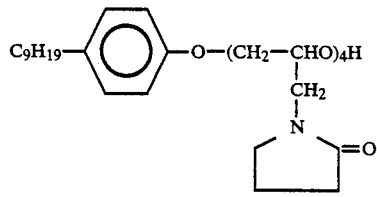

EXAMPLE 4

Reaction Product of Nonylphenol with 6 Moles Epoxypropyl Pyrrolidone To a 500 ml. round bottom flask equipped with a reflux condenser, stirrer, dropping funnel, and nitrogen bubbler was charged 29.0 g. (0.13M) nonylphenol and 0.1 g. of powdered potassium hydroxide. The mixture was heated to 110° to 120° C. with a nitrogen purge to remove water. The purge was carried out prior to placing the condenser on the reactor. The temperature was held at 110° to 120° C. for 2 hours under the nitrogen purge. Epoxypropyl pyrrolidone 112.0 g. (0.79M) was added dropwise over a 2-hour period, holding the temperature at 130° to 135° C. The reaction was held at 130° to 140° C. for two hours after the addition was completed. Vapor phase chromatography indicated the absence of epoxypropyl pyrrolidone and nonylphenol. The reaction mixture was cooled to 65° C. and neutralized with glacial acetic acid. The product was clear in water and had a cloud point of 66° C. (1% in 10% sodium chloride). Analysis by ultraviolet spectroscopy indicated that 7 moles of epoxide had reacted. The product is defined by the formula:

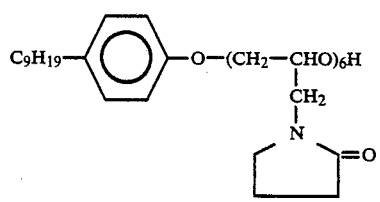

EXAMPLE 5

Reaction Product of Nonylphenol-4 Ethylene Oxide adduct with 2 Moles Epoxypropyl Pyrrolidone To a 500 ml. round bottom flask equipped with a reflux condenser, stirrer, dropping funnel, and nitrogen bubbler was charged 154.0 g. (0.39M) Igepal CO430 (the reaction product of 1 mole nonylphenol +4 moles of ethylene oxide) and 0.1 g. of powdered potassium hydroxide. The mixture was heated to 110°-120° C. with a nitrogen purge to remove water. The purge was carried out prior to placing the condenser on the reactor. The temperature was held at 110° to 120° C. for 2 hours under the nitrogen purge. Epoxypropyl pyrrolidone 112.0 g. (0.79M) was added dropwise over a 2-hour period, while holding the temperature at 130°-135° C. The reaction was held at 130°-140° C. for two hours after the addition was completed. Vapor phase chromatography indicated the absence of epoxypropyl pyrrolidone. The reaction mixture was cooled to 65° C. and neutralized with glacial acetic acid. The product was cloudy in water and had a cloud point below zero.

Product corresponds to following formula 5 where m is 4 and n is 2

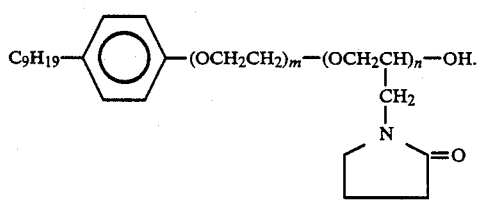

5

EXAMPLE 6

Reaction Product of Nonylphenol +4 Ethylene Oxide Adduct with 4 Moles Epoxypropyl Pyrrolidone To a 500 ml. round bottom flsk equipped with a reflux condenser, stirrer, dropping funnel, and nitrogen bubbler was charged 78.2 g. (0.19M) Igepal C0430 and 0.1 g. of powdered potassium hydroxide. The mixture was heated to 110°-120° C. with a nitrogen purge to remove water. The purge was carried out prior to placing the condenser on the reactor. The temperature was held at 110° to 120° C. for 2 hours under the nitrogen purge. Epoxypropyl pyrrolidone 112.0 g. (0.79M) was added dropwise over a 2-hour period, while holding the temperature at 130°-135° C. The reaction was held at 130°-140° C. for two hours after the addition was completed. Vapor phase chromatography indicated the absence of epoxypropyl pyrrolidone. The reaction mixture was cooled to 65° C. and neutralized with glacial acetic acid. The product was clear in water and had a cloud point over 100° C. in water.

The formula of the product corresponds to that of Example 5 wherein m is 4 and n is 4.

EXAMPLE 7

Reaction Product of Nonylphenol-15 ethylene Oxide Adduct with 3.5 moles Epoxypropyl Pyrrolidone To a 500 ml. round bottom flask equipped with a reflux condenser, stirrer, dropping funnel, and nitrogen bubbler was charged 198 g. (0.22M) Igepal CO730 (nonylphenol +15 ethylene oxide) and 0.1 g. of powdered potassium hydroxide. The mixture was heated to 110°-120° C. with a nitrogen purge to remove water. The purge was carried out prior to placing the condenser on the reactor. The temperature was held at 110°-120° C. for 2 hours under the nitrogen purge. Epoxypropyl pyrrolidone 112.0 g. (0.79M) was added dropwise over a 2-hour period, while holding the temperature at 130°-135° C. The reaction was held at 130°-140° C. for two hours after the addition was completed. Vapor phase chromatography indicated the absence of epoxypropyl pyrrolidone. The reaction mixture was cooled to 65° C. and neutralized with glacial acetic acid. The product was clear in water and had a cloud point over 100° C. in water.

The formula of the product corresponds to that of Example 5 wherein m is 15 and n is 3.5.

EXAMPLE 8

Reaction Product of Dodecanol with 5 Moles Epoxypropyl Pyrrolidone To a 500 ml. round bottom flask equipped with a reflux condenser, stirrer, dropping funnel, and nitrogen bubbler was charged 29.3 g. (0.16M) Dodecanol and 0.1 g. of powdered potassium hydroxide. The mixture was heated to 110°-120° C. with a nitrogen purge to remove ater. The purge was carried out prior to placing the condenser on the reactor. The temperature was held at 110°-120° C. for 2 hours under the nitrogen purge. Epoxypropyl pyrrolidone 112.0 g. (0.79M) was added dropwise over a 2-hour period, holding the temperature at 130°-135° C. The reaction was held at 130°-140° C. for two hours after the addition was completed. Vapor phase chromatography indicated the absence of epoxypropyl pyrrolidone and dodecanol. The acetic acid. The product was clear in water, reaction mixture was cooled to 65° C. and neutralized with glacial a cloud point of 67-68° C. (1% in 10% sodium chloride solution). Product corresponds to formula

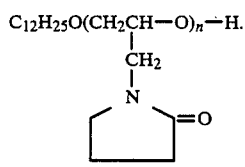

6 where n is 5.

EXAMPLE 9

Reaction Product of Dodecanol with 3 Moles Epoxypropyl Pyrrolidone

To a 500 ml. round bottom flask equipped with a reflux condenser, stirrer, dropping funnel, and nitrogen bubbler was charged 49.0 g. (0.26M) Dodecanol and 0.1 g. of powdered potassium hydroxide. The mixture was heated to 110°-120° C. with a nitrogen purge to remove water. The purge was carried out prior to placing the condenser on the reactor. The temperature was held at 110°-120° C. for 2 hours under the nitrogen purge. Epoxypropyl pyrrolidone 112.0 g. (0.79M) was added dropwise over a 2-hour period, holding the temperature at 130°-135° C. The reaction was held at 130°-140° C. for two hours after the addition was completed. Vapor phase chromatography indicated the absence of epoxypropyl pyrrolidone and dodecanol. The reaction mixture was cooled to 65° C. and neutralized with glacial acetic acid. The product was cloudy in water and had a cloud point below zero.

The formula of the product of this Example corresponds to that of Example 8 where n is 3.

EXAMPLE 10

Reaction Product of Dinonylphenol with 4 Moles Epoxypropyl Pyrrolidone

To a 500 ml. round bottom flask equipped with a reflux condenser, stirrer, dropping funnel, and nitrogen bubbler was charged 65.7 g. (0.19M) Dinonylphenol and 0.1 g. of powdered potassium hydroxide. The mixture was heated to 110°–120° C. with a nitrogen purge to remove water. The purge was carried out prior to placing the condenser on the reactor. The temperature was held at 110°–120° C. for 2 hours under the nitrogen purge. Epoxypropyl pyrrolidone 112.0 g. (0.79M) was added dropwise over a 2-hour period, holding the temperature at 130°–135° C. The reaction was held at 130°–140° C. for two hours after the addition was completed. The reaction mixture was cooled to 65° C. and neutralized with glacial acetic acid. The product was clear in water and is defined by the formula

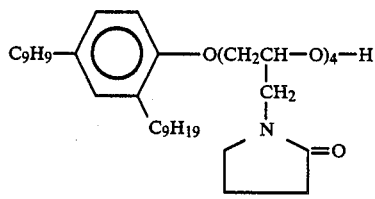

EXAMPLE 11

Reaction Product of Nonylphenol-3-Propylene

Oxide Adduct with 4 Moles Epoxypropyl Pyrrolidone

To a 500 ml. round bottom flask equipped with a reflux condenser, stirrer, dropping funnel, and nitrogen bubbler was charged 77.8 g. (0.19M) nonylphenol 3 propylene oxide adduct and 0.1 g. of powdered potassium hydroxide. The mixture was heated to 110°–120° C. with a nitrogen purge to remove water. The purge was carried out prior to placing the condenser on the reactor. The temperature was held at 110°–120° C. for 2 hours under the nitrogen purge. Epoxypropyl pyrrolidone 112.0 g. (0.79M) was added dropwise over a 2-hour period, holding the temperature at 130°–135° C. The reaction was held at 130°–140° C. for two hours after the addition was completed. The reaction mixture was cooled to 65° C. and neutralized with glacial acetic acid.

The product corresponds to formula

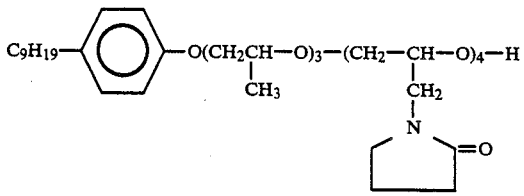

EXAMPLE 12

Product of Reaction Nonylphenol with 4 Moles of Epoxypropylpyrrolidone and 3 Moles of Propylene Oxide The product of Example 3 is reacted with 3 moles propylene oxide. To 78.4 g. (0.1 moles) of Example 3 is added 0.9 g. of potassium hydroxide and 17.4 g (0.3 moles) of propylene oxide at a temperature of 115° to 120° C. and 85 psig. After reaction is completed it is neutralized with glacial acetic acid. The product corresponds to the formula

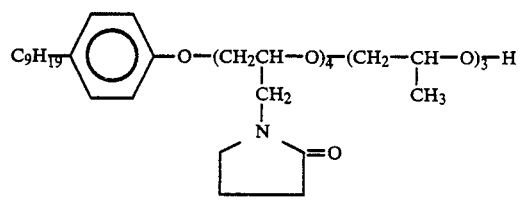

The preparation of the following compounds, based on the glycidylether of hydroxyethylpyrrolidone, correspond to the general formula:

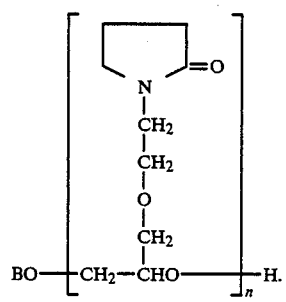

7

EXAMPLE 13

Reaction Product of Hydroxyethyl Pyrrolidone with Epichlorohydrin

To a 2 liter, 4-neck flask equipped with a stirrer, reflux condenser, thermometer and dropping funnel was added 50% aq. sodium hydroxide (534 ml.), epichlorohydrin (334 ml.), and tetrabutyl ammonium hydrogen sulphate (11.2 g.).

The reaction was stirred at room temperature for 15 minutes, after which hydroxyethyl pyrrolidone (117 ml., 1 mole) was added dropwise over a period of 2 hours. Reaction became exothermic and the temperature was maintained between 40–60° C. using an ice-water bath. The reaction mixture was stirred overnight (total stirring 24 hours) at room temperature and then poured in a cold saturated sodium chloride solution (aoprox. 1 liter), extracted with ethyl acetate (4×300 ml.). The combined ethyl acetate extracts were dried over anhydrous sodium sulphate, filtered and the removal of the solvent gave the crude product (260.1 g.). Removal of low-boiling impurities at 60–80° C. (0.5 mm Hg) and then distillation of the desired epoxide was achieved at 131° C. (0.1 mm Hg). The yield was 111.3 g., (61%) and the product was a colorless, pale yellow liquid. The product purity measured by GC was 97.3%; by wet analysis 94.7%.

EXAMPLE 14

Reaction Product of Glycidylether of Hydroxyethyl Pyrrolidone with Lauryl Alcohol To a 250 ml., 4-neck flask equipped with a stirrer, reflux condenser, dropping funnel and thermometer was added lauryl alcohol (9.3 g., 0.05 mole) and potassium hydroxide (powder, 1 g. 0.018 mole). The mixture was heated to 120-160° C. after which glycidylether of hydroxyethyl pyrrolidone (37 g., 0.2 mole) was added dropwise over a period of 2.5 hours. A nitrogen blanket was maintained over the resulting reaction mass throughout the reaction period. After the epoxide addition was completed, the reaction mass was stirred at 120-160° C. for an additional 2 hours and then allowed to cool to room temperature. The reaction mass was then dissolved in $CH_2Cl_2$ (100-200 ml) and sodium dihydrogen phosphate was added to the solution to deactivate the catalyst. The $CH_2Cl_2$ solution was then dried over sodium sulphate, filtered and the solvent is removed to give a dark colored thick syrup. The product yeild was nearly quantitative The product had a cloud point (1% in water) of 53° C. The product of this Example corresponds to the foregoing formula 7 where n is 4 and B is $-C_{12}H_{25}$.

EXAMPLE 15

Reaction Product of Glycidylether of Hydroxyethyl Pyrrolidone with Lauryl Alcohol To a 250 ml., 4-neck flask equipped with a stirrer, reflux condenser, dropping funnel and thermometer was added lauryl alcohol (9.3 g., 0.05 mole) and potassium hydroxide (powder, 1 g. 0.018 mole). The mixture was heated to 120°-160° C. after which glycidylether of hydroxyethyl pyrrolidone (55.5 g., 0.3 mole) was added dropwise over a period of 2.5 hours. A nitrogen blanket was maintained over the resulting reaction mass throughout the reaction period. After the epoxide addition was completed, the reaction mass was stirred at 120°-160° C. for an additional 2 hours and then allowed to cool to room temperature. The reaction mass was dissolved in $CH_2Cl_2$ (100-200 ml.) and sodium dihydrogen phosphate was added to the solution to deactivate the catalyst. The $CH_2Cl_2$ solution was then dried over sodium sulphate, filtered and the solvent was removed to give a dark colored thick syrup. The product yield was nearly quantitative. The product has a cloud point of 87° C. (1% in 10% sodium chloride) and corresponds to foregoing formula 7 wherein n is 6 and B is $-C_{12}H_{25}$.

EXAMPLE 16

Reaction Product of 4 Glycidylether of Hydroxyethyl Pyrrolidone with Nonyl Phenol To a 250 ml., 4-neck flask equipped with a stirrer, reflux condenser, dropping funnel and thermometer was added nonyl phenol (11 g., 0.05 mole) and potassium hydroxide (powder, 1 g. 0.018 mole). The mixture was heated to 120°-160° C. after which glycidylether of hydroxyethyl pyrrolidone (37 g., 0.2 mole) was added dropwise over a period of 2.5 hours. A nitrogen blanket was maintained over the resulting reaction mass throughout the reaction period. After the epoxide addition was completed, the reaction mass was stirred at 120°-160° C. for an additional 2 hours and then allowed to cool to room temperature. The reaction mass was dissolved in $CH_2Cl_2$ (100-200 ml.) and sodium dihydrogen phosphate was added to the solution to deactivate the catalyst. The $CH_2Cl_2$ solution was then dried over sodium sulphate, filtered and the solvent was removed to give a dark colored thick syrup. The product yield was nearly quantitative. The product having a cloud point of 78° C. (1% in water), corresponds to foregoing formula 7 wherein n is 4 and B is $-C_9H_{19}$.

EXAMPLE 17

Reaction Product of 6 Glycidylether of Hydroxyethyl Pyrrolidone with Nonyl Phenol To a 250 ml., 4-neck flask equipped with a stirrer, reflux condenser, dropping funnel and thermometer was added nonyl phenol (11 g., 0.05 mole) and potassium hydroxide (powder, 1 g. 0.018 mole). The mixture was heated to 120°-160° C. after which glycidylether of hydroxyethyl pyrrolidone (55.5 g., 0.3 mole) was added dropwise over a period of 2.5 hours. A nitrogen blanket was maintained over the resulting reaction mass throughout the reaction period. After the epoxide addition was completed, the reaction mass was stirred at 120°-160° C. for an additional 2 hours and then allowed to cool to room temperature. The reaction mass was dissolved in $CH_2Cl_2$ (100-200 ml.) and sodium dihydrogen phosphate was added to the solution to deactivate the catalyst. The $CH_2Cl_2$ solution was then dried over sodium sulphate, filtered and the solvent was removed to give a dark colored thick syrup. The product yield was nearly quantitative. The product having a cloud point of 77° C. (1% in 10% sodium chloride), corresponds to foregoing formula 7 wherein n is 6 and B is $-C_9H_{19}$.

EXAMPLE 18

The surface tension in dynes/cm using a Fisher Surface Tensiomat (Model #21, Du Nouy Tensiometer) was determined for product samples of this invention in aqueous solutions at 25° C. ±1°. The results are reported in following Table I.

Part A of the Table refers to surfactants having the general formula

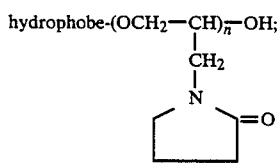

whereas Part B of the Table refers to surfactants having the general formula

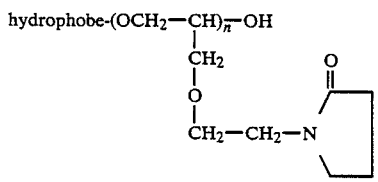

TABLE I

| | SURFACE TENSION OF AQUEOUS SOLUTIONS (DYNES/CM) | | | | | | |
|---|---|---|---|---|---|---|---|
| | | | Concentration in Distilled Water (%) | | | | |
| Sample | Hydrophobe Moiety | n | 1.0 | 0.1 | 0.01 | 0.001 | CMC $\times 10^{-2}$** |
| | A. | | | | | | |
| A | $C_{12}H_{25}$ | 3 | 26.6 | 26.8 | 26.5 | 49.0 | 1.02 |
| B | $C_{12}H_{25}$ | 5 | 33.1 | 32.6 | 40.2 | 58.2 | 1.25 |
| C | $C_9H_{19}-C_6H_4$ | 4 | 30.3 | 30.9 | 31.2 | 47.5 | 0.94 |
| D | $C_9H_{19}-C_6H_4$ | 6 | 33.9 | 34.2 | 38.4 | 56.2 | 1.4 |
| E | $C_9H_{19}-C_6H_4-(OCH_2CH_2)_4$ | 2 | 30.6 | 31.9 | 31.8 | 46.2 | 1.0 |
| F | $C_9H_{19}-C_6H_4-(OCH_2CH_2)_4$ | 4 | 30.6 | 30.7 | 32.5 | 48.2 | 1.4 |
| G | $C_9H_{19}-C_6H_4-(OCH_2CH_2)_{15}$ | 3.5 | 38.4 | 38.8 | 41.1 | 52.6 | 1.4 |
| | B. | | | | | | |
| J | $C_{12}H_{25}$ | 2 | 27.5 | 28.4 | 31.8 | 35.8 | — |
| K | $C_{12}H_{25}$ | 4 | 29.3 | 29.6 | 36.2 | 52.4 | — |
| L | $C_{12}H_{25}$ | 6 | 36.8 | 37.0 | 40.5 | 54.2 | — |
| M | $C_9H_{19}-C_6H_4$ | 2 | 33.3 | 33.5 | 34.1 | 49.7 | — |
| N | $C_9H_{19}-C_6H_4$ | 4 | 33.9 | 34.9 | 36.2 | 49.9 | — |
| O | $C_9H_{19}-C_6H_4$ | 6 | 40.0 | 40.0 | 41.9 | 58.6 | — |
| P | Igepal CO-530*** | — | 27.0* | 27.4* | 28.0 | 23.0 | — |

*cloudy solution
**Critical Micelle Concentration $\times 10^{-2}$
***$C_9H_{19}-C_6H_4-(OCH_2CH_2)_5OH$ The above results, Part A, indicate that the surfactant properties of the products, while still highly active, tend to decrease as the moles of oxypropyl pyrrolidone increase. The above data also indicates that the oxypropylpyrrolidone moiety has much greater solubilizing capactiy than an ethylene oxide adduct since

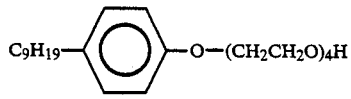

(Igepal CO-430) is water insoluble; whereas the above A products containing the hydrophobe $C_9H_{19}-C_6H_4-(OCH_2CH_2)_4$ are completely soluble in water.

EXAMPLE 19

Ross Miles Foam Test

In a mm graduated glass column, 0.1% aqueous solutions of the samples of the present invention were tested as antifoaming agents at 25° C. ±1°. The results of these tests are reported in Table II. As in the above example, Part A refers to compounds having the general formula:

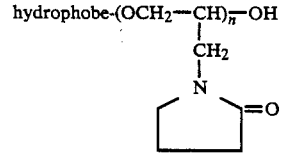

whereas Part B refers to compounds having the general formula:

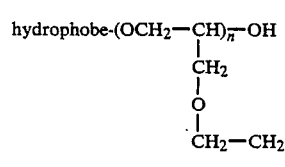

TABLE II

| Sample | Hydrophobe Moiety | n | Foam Height mm initial | Foam Height mm after 5 Minutes |
|---|---|---|---|---|
| | A. | | | |
| A | $C_{12}H_{25}$ | 3 | 63.5 | 54.5 |
| B | $C_{12}H_{25}$ | 5 | 18.0 | 9.0 |
| C | $C_9H_{19}-C_6H_4$ | 4 | 32.5 | 30.0 |
| D | $C_9H_{19}-C_6H_4$ | 6 | 40.5 | 38.0 |
| E | $C_9H_{19}-C_6H_4-(OCH_2CH_2)_4$ | 2 | 26.0 | 17.5 |
| F | $C_9H_{19}-C_6H_4-(OCH_2CH_2)_4$ | 4 | 15.0 | 4.5 |
| G | $C_9H_{19}-C_6H_4-(OCH_2CH_2)_{15}$ | 3.5 | 81.0 | 71.0 |
| H | Igepal CO-730* | — | 130.0 | 110.0 |
| | B. | | | |
| J | $C_{12}H_{25}$ | 2 | 15.5 | 15.5 |
| K | $C_{12}H_{25}$ | 4 | 34.5 | 24.0 |
| L | $C_{12}H_{25}$ | 6 | 62.6 | 23.5 |
| M | $C_9H_{19}-C_6H_4$ | 2 | 14.5 | 10.0 |
| N | $C_9H_{19}-C_6H_4$ | 4 | 35.0 | 27.5 |
| O | $C_9H_{19}-C_6H_4$ | 6 | 52.5 | 22.5 |
| P | Igepal CO-530 | — | 15.0 | 10.0 |

*$C_9H_{19}-C_6H_4O(CH_2CH_2O)_{15}-H$

All of the present products are low foamers although samples in Part A having the hydrophobe $C_{12}H_{25}-$ wherein n is 5 and having the hydrophobe $C_9H_{19}-C_6H_4-(OCH_2CH_2)_4-$ wherein n is 4 have outstanding antifoaming properties. Preferred antifoaming agents of the block copolymer type in this invention generally contain

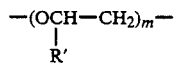

moieties wherein m has a value of from 4 to 10.

Contrary to the di- and tetra- ethyleneoxide nonylphenyl surfactants which show a decrease in foaming with increasing moles of ethylene oxide, the present compounds show increasing sudsing with increasing moles of ethylene oxide.

It was also found that, upon addition of 3.5 moles of Sample B to Igepal CO-730, the initial and final foam heights were reduced by at least 2 fold.

EXAMPLE 20

Waring Blender Foam Test

Aqueous solutions (200 ml of 1% distilled water solutions) of the samples reported in Table III were made up in 500 ml glass beakers. The solutions were stirred for 30 minutes with a single speed Waring Blender (21,000 rpm) at 25° C. ±1°. The resulting foam heights were recorded and reported below in Table III.

As in the preceding Tables, Part A refers to compounds having the oxypropyl pyrrolidone structure; whereas those in Part B refers to the compounds having the glycidol ether pyrrolidone structure.

TABLE III

| Sample | Hydrophobe Moiety | n | Foam Height mm initial | Foam Height mm after 5 minutes |
|---|---|---|---|---|
| | A. | | | |
| A | $C_{12}H_{25}$ | 3 | 70.5 | 63.5 |
| C | $C_9H_{19}$—$C_6H_4$ | 4 | 31.5 | 28.5 |
| D | $C_9H_{19}$—$C_6H_4$ | 6 | 77.0 | 48.0 |
| E | $C_9H_{19}$—$C_6H_4$—$(OCH_2CH_2)_4$ | 2 | 30.5 | 28.0 |
| F | $C_9H_{19}$—$C_6H_4$—$(OCH_2CH_2)_4$ | 4 | 33.5 | 30.0 |
| G | $C_9H_{19}$—$C_6H_4$—$(OCH_2CH_2)_{15}$ | 3.5 | 67.5 | 60.0 |
| H | Igepal CO-730 | — | 82.0 | 73.0 |
| | B. | | | |
| L | $C_{12}H_{25}$ | 6 | 68.0 | 40.0 |
| O | $C_9H_{19}$—$C_6H_4$ | 6 | 70.0 | 30.0 |

EXAMPLE 21

Drave's Wetting Test This test was conducted on a 5 gram cotton skein weighted with a 3.0 gram hook. The time in seconds required for the yarn to sink into 0.1% and 0.50% distilled water solutions of the present products was recorded and is reported in following Table IV.

TABLE IV

| Sample | | | Wetting Out Time (Sec.) | |
|---|---|---|---|---|
| | hydrophobe | n | 0.1% Conc. | 0.5% Conc. |
| Part A | | | | |
| A | $C_{12}H_{25}$ | 3 | 17.2 | — |
| B | $C_{12}H_{25}$ | 5 | 127.0 | — |
| C | $C_9H_{19}$—$C_6H_4$ | 4 | 11.2 | — |
| D | $C_9H_{19}$—$C_6H_4$ | 6 | 40.6 | — |
| E | $C_9H_{19}$—$C_6H_4(OCH_2CH_2)_4$ | 2 | 27.0 | — |
| F | $C_9H_{19}$—$C_6H_4(OCH_2CH_2)_4$ | 4 | 36.0 | — |
| G | $C_9H_{19}$—$C_6H_4(OCH_2CH_2)_{15}$ | 3.5 | 41.9 | — |
| Part B | | | | |
| J | $C_{12}H_{25}$ | 2 | 101.5 | — |
| K | $C_{12}H_{25}$ | 4 | 136.1 | 7.1 |
| L | $C_{12}H_{25}$ | 6 | >300.0 | 54.6 |
| M | $C_9H_{19}C_6H_4$ | 2 | >72.0 | 25.6 |
| N | $C_9H_{19}C_6H_4$ | 4 | 47.9 | 8.3 |
| O | $C_9H_{19}C_6H_4$ | 6 | >300.0 | 54.6 |
| P | Igepal CO-530 | — | 29.5 | — |

All of the above except Sample B, Part A, and J, K, L and 0, Part B, are considered to have good wetting properties.

Because of their good wetting and low foaming properties, Samples A, C, and F are particularly useful adjuvants for hard surface cleaners, low foaming laundry detergents, metal cleaners, etching solutions, anti-rust compositions, etc.

EXAMPLE 22

The present products were tested for solubility in a wide range of chemicals. In each case a 10% solubility level was used for testing at 25° C. ±1°. The results of these tests are reported in following Table V.

TABLE V

| | Part A | | | | | |
|---|---|---|---|---|---|---|
| Hydrophobe-n | $C_{12}H_{25}$ —3 | $C_{12}H_{25}$ —5 | $C_9H_{19}C_6H_4$ —2 | $C_9H_{19}C_6H_4$ —4 | $C_9H_{19}C_6H_4$ —6 | $C_9H_{19}C_6H_4$—$(OCH_2CH_2)_4$ —2 |
| Test Solvent | | | | | | |
| water | S | S | PS | S | S | S |
| ethanol | S | S | S | S | S | S |
| butyl cellosolve | S | S | S | S | PS | S |
| xylene | S | — | S | S | — | I |
| perchloroethylene | S | I | S | S | — | S |
| kerosene | I | I | PS | I | — | I |

TABLE V-continued

|  |  |  |  |  |  |  |
|---|---|---|---|---|---|---|
| mineral oil | I | I | D | I | — | I |
| heptane | I | I | PS | I | — | I |

| | Part A | |
|---|---|---|
| Hydrophobe-n | $C_9H_{19}C_6H_4$—$(OCH_2CH_2)_4$ —4 | $C_9H_{19}C_6H_4$—$(OCH_2CH_2)_{15}$ —3.5 |
| Test Solvent | | |
| water | S | S |
| ethanol | S | S |
| butyl cellosolve | S | S |
| xylene | D | S |
| perchloroethylene | I | S |
| kerosene | I | PS |
| mineral oil | I | PS |
| heptane | I | D |

| | Part B | | | | | |
|---|---|---|---|---|---|---|
| Hydrophobe-n | $C_{12}H_{25}$ —2 | $C_{12}H_{25}$ —4 | $C_{11}H_{25}$ —6 | $C_9H_{19}C_6H_4$ —2 | $C_9H_{19}C_6H_4$ —4 | $C_9H_{19}C_6H_4$ —6 |
| Test Solvent | | | | | | |
| water | PS | S | S | S | S | S |
| acetone | S | S | S | S | S | S |
| isopropanol | S | S | S | S | S | S |
| xylene | PS | PS | PS | PS | S | PS |
| heptane | PS | I | I | I | I | I |
| mineral spirits | I | I | I | I | I | I |
| petroleum ether | I | I | I | I | I | I |

S = soluble; PS = partially soluble; D = dispersable and I = insoluble

Generally, the above products are soluble in polar solvents but only partly soluble or insoluble in non-polar solvents.

The above Examples 13–17 provide specific embodiments of the invention; however, it is to be understood that any of the remaining species disclosed herein provide comparable surface activity and low foaming properties and that these, as well as those specifically illustrated above, can be incorporated into formulations or complexed with water insoluble chemicals to produce valuable products.

What is claimed is:

1. A compound having the formula:

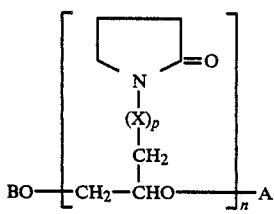

wherein

X is

—$(CH_2)_s$— or —$(CH_2)_s$—O—;

B is $C_{8-24}$ alkyl- $C_{8-24}$alkyl—$(OCH_2$—$\underset{R'}{CH})_m$—;

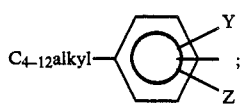

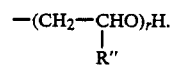

Y and Z are each H or $C_{1-12}$ alkyl;
m is an integer having a value of 1 to 100;
n is an integer having a value of 2 to 50;
p is an integer having a value of 0 or 1;
s is an integer having a value of 1 or 2;
R' is H of $CH_3$ and A is H or —$(CH_2$—$\underset{R''}{CHO})_r$H.

2. The compound of claim 1 having the formula

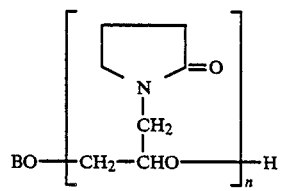

wherein n has a value of from 2 to 50 and B is selected from the group consisting of $C_9$ to $C_{14}$ alkyl and $C_8$ to $C_{12}$ alkylphenyl wherein phenyl is optionally substituted with up to two additional alkyl groups each containing from 1 to 12 carbon atoms.

3. The compound of claim 1 having the formula

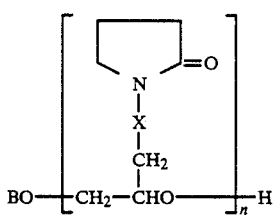

wherein n has a value of from 2 to 50, B is selected from the group consisting of $C_9$ to $C_{14}$ alkyl and $C_8$ to $C_{12}$ alkylphenyl wherein phenyl is optionally substituted with up to two additional alkyl groups containing from 1 to 12 carbon atoms and X is as defined in claim 1.

4. The compound of claim 1 wherein B is selected from the group consisting of

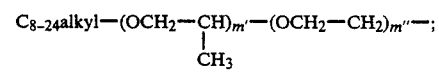

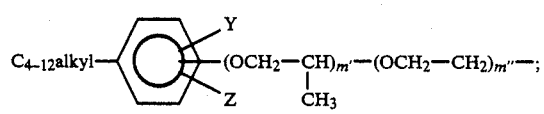

-continued

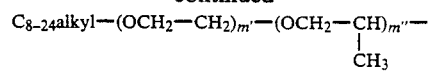

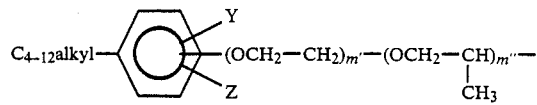

wherein m' and m'' are integers each having a value of from 3 to 50.

5. The composition comprising between about 0.001 wt. % and about 50 wt. % of the compound of claim 1 in an inert solvent.

6. The composition comprising between about 0.001 wt. % and about 50 wt. % of the compound of claim 2 in an inert carrier.

7. The composition comprising between about 0.001 wt. % and about 50 wt. % of the compound of claim 3 in an inert carrier.

8. The composition comprising between about 0.001 wt. % and about 50 wt. % of the compound of claim 4 in an inert carrier.

9. The composition of claim 5 wherein the solvent is water.

10. The composition comprising between about 0.0001 and about 0.05 wt. % of the compound of claim 1 and a liquid mixture having a high surface tension.

* * * * *